US007578673B2

(12) United States Patent
Wen et al.

(10) Patent No.: US 7,578,673 B2
(45) Date of Patent: Aug. 25, 2009

(54) SYSTEM AND METHODS FOR COMBINATION TREATMENTS OF DENTAL PATIENTS

(75) Inventors: Huafeng Wen, Redwood Shores, CA (US); Eric Kuo, Foster City, CA (US); Amir Abolfathi, Menlo Park, CA (US); Loc X. Phan, San Jose, CA (US); Peter G. Knopp, Palo Alto, CA (US)

(73) Assignee: Align Technology, Inc., Santa Clara, CA (US)

( * ) Notice: Subject to any disclaimer, the term of this patent is extended or adjusted under 35 U.S.C. 154(b) by 0 days.

(21) Appl. No.: 10/870,689

(22) Filed: Jun. 17, 2004

(65) Prior Publication Data

US 2005/0064360 A1    Mar. 24, 2005

Related U.S. Application Data

(63) Continuation of application No. 10/375,224, filed on Feb. 26, 2003, now abandoned.

(51) Int. Cl.
*A61C 3/00* (2006.01)

(52) U.S. Cl. ........................................................ 433/24

(58) Field of Classification Search .................. 433/24, 433/29, 6, 3; 29/896.1, 896.11
See application file for complete search history.

(56) References Cited

U.S. PATENT DOCUMENTS

| 2,467,432 A | 4/1949 | Kesling |
| 3,660,900 A | 5/1972 | Andrews |
| 3,860,803 A | 1/1975 | Levine |
| 3,916,526 A | 11/1975 | Schudy |
| 3,949,478 A | 4/1976 | Schinhammer |
| 3,950,851 A | 4/1976 | Bergersen |
| 4,014,096 A | 3/1977 | Dellinger |
| 4,160,322 A * | 7/1979 | Frazier ........................ 433/24 |
| 4,195,046 A | 3/1980 | Kesling |
| 4,324,546 A | 4/1982 | Heitlinger et al. |
| 4,348,178 A | 9/1982 | Kurz |
| 4,478,580 A | 10/1984 | Barrut |
| 4,501,554 A | 2/1985 | Hickham et al |

(Continued)

FOREIGN PATENT DOCUMENTS

EP    0091876 A1    10/1983

(Continued)

OTHER PUBLICATIONS

Orametrix, Inc., "Treatment Planning Software" (Dec. 10, 2002) pp. 1-2.

(Continued)

*Primary Examiner*—Ralph A Lewis
(74) *Attorney, Agent, or Firm*—Townsend and Townsend and Crew LLP

(57) ABSTRACT

Systems and methods for fabricating a dental template to position an object on a patient's tooth to move the tooth from an initial position to a target position are disclosed. The system digitizes a model of the patient's tooth at the initial position; places an object on the tooth model at the target position; determines the position of the object at the initial position; and fabricates the dental template to locate the object on the patient's tooth.

23 Claims, 10 Drawing Sheets

U.S. PATENT DOCUMENTS

| | | | |
|---|---|---|---|
| 4,504,225 A | 3/1985 | Yoshii | |
| 4,505,673 A | 3/1985 | Yoshii | |
| 4,526,540 A | 7/1985 | Dellinger | |
| 4,551,096 A * | 11/1985 | Dellinger | 433/24 |
| 4,575,805 A | 3/1986 | Moermann et al. | |
| 4,611,288 A | 9/1986 | Duret et al. | |
| 4,656,860 A | 4/1987 | Orthuber et al. | |
| 4,663,720 A | 5/1987 | Duret et al. | |
| 4,742,464 A | 5/1988 | Duret et al. | |
| 4,755,139 A | 7/1988 | Abbatte et al. | |
| 4,763,791 A | 8/1988 | Halverson et al. | |
| 4,793,803 A | 12/1988 | Martz | |
| 4,798,534 A | 1/1989 | Breads | |
| 4,812,118 A | 3/1989 | Creekmore et al. | |
| 4,837,732 A | 6/1989 | Brandestini et al. | |
| 4,850,864 A | 7/1989 | Diamond | |
| 4,856,991 A | 8/1989 | Breads et al. | |
| 4,936,862 A | 6/1990 | Walker et al. | |
| 4,937,928 A | 7/1990 | van der Zel | |
| 4,964,770 A | 10/1990 | Steinbichler et al. | |
| 4,975,052 A | 12/1990 | Spencer et al. | |
| 5,011,405 A | 4/1991 | Lemchen | |
| 5,017,133 A | 5/1991 | Miura | |
| 5,027,281 A | 6/1991 | Rekow et al. | |
| 5,035,613 A | 7/1991 | Breads et al. | |
| 5,055,039 A | 10/1991 | Abbatte et al. | |
| 5,059,118 A | 10/1991 | Breads et al. | |
| 5,100,316 A | 3/1992 | Wildman | |
| 5,121,333 A | 6/1992 | Riley et al. | |
| 5,128,870 A | 7/1992 | Erdman et al. | |
| 5,131,843 A | 7/1992 | Hilgers et al. | |
| 5,131,844 A | 7/1992 | Marinaccio et al. | |
| 5,139,419 A | 8/1992 | Andreiko et al. | |
| 5,144,339 A * | 9/1992 | Ohashi et al. | 347/261 |
| 5,184,306 A | 2/1993 | Erdman et al. | |
| 5,186,623 A | 2/1993 | Breads et al. | |
| 5,257,203 A | 10/1993 | Riley et al. | |
| 5,273,429 A | 12/1993 | Rekow et al. | |
| 5,278,756 A | 1/1994 | Lemchen et al. | |
| 5,338,198 A | 8/1994 | Wu et al. | |
| 5,340,309 A | 8/1994 | Robertson | |
| 5,342,202 A | 8/1994 | Deshayes | |
| 5,368,478 A | 11/1994 | Andreiko et al. | |
| 5,382,164 A | 1/1995 | Stern | |
| 5,395,238 A | 3/1995 | Andreiko et al. | |
| 5,431,562 A | 7/1995 | Andreiko et al. | |
| 5,440,496 A | 8/1995 | Andersson et al. | |
| 5,447,432 A | 9/1995 | Andersson et al. | |
| 5,452,219 A | 9/1995 | Dehoff et al. | |
| 5,454,717 A | 10/1995 | Andreiko et al. | |
| 5,456,600 A | 10/1995 | Andreiko et al. | |
| 5,474,448 A | 12/1995 | Andreiko et al. | |
| RE35,169 E * | 3/1996 | Lemchen et al. | 433/24 |
| 5,518,397 A * | 5/1996 | Andreiko et al. | 433/24 |
| 5,533,895 A | 7/1996 | Andreiko et al. | |
| 5,542,842 A | 8/1996 | Andreiko et al. | |
| 5,549,476 A | 8/1996 | Stern | |
| 5,587,912 A | 12/1996 | Andersson et al. | |
| 5,605,459 A | 2/1997 | Kuroda et al. | |
| 5,607,305 A | 3/1997 | Andersson et al. | |
| 5,645,421 A | 7/1997 | Slootsky | |
| 5,655,653 A | 8/1997 | Chester | |
| 5,683,243 A * | 11/1997 | Andreiko et al. | 433/3 |
| 5,733,126 A | 3/1998 | Andersson et al. | |
| 5,740,267 A | 4/1998 | Echerer et al. | |
| 5,791,896 A * | 8/1998 | Ipenburg | 433/3 |
| 5,971,574 A | 10/1999 | Taniuchi et al. | |
| 5,971,754 A | 10/1999 | Sondhi et al. | |
| 5,975,893 A * | 11/1999 | Chishti et al. | 433/6 |
| 6,123,544 A * | 9/2000 | Cleary | 433/24 |
| 6,210,162 B1 * | 4/2001 | Chishti et al. | 433/213 |
| 6,296,481 B1 | 11/2001 | Kyung et al. | |
| 6,315,553 B1 | 11/2001 | Sachdeva et al. | |
| 6,464,496 B1 | 10/2002 | Sachdeva et al. | |
| 6,540,512 B1 | 4/2003 | Sachdeva et al. | |
| 6,554,613 B1 * | 4/2003 | Sachdeva et al. | 433/24 |
| 6,632,089 B2 | 10/2003 | Rubbert et al. | |
| 6,648,640 B2 * | 11/2003 | Rubbert et al. | 433/24 |
| 6,905,337 B1 * | 6/2005 | Sachdeva | 433/229 |
| 6,918,761 B2 | 7/2005 | Sachdeva | |
| 7,056,115 B2 * | 6/2006 | Phan et al. | 433/24 |
| 7,137,812 B2 | 11/2006 | Cleary et al. | |
| 7,252,509 B2 | 8/2007 | Sachdeva | |
| 2002/0010568 A1 | 1/2002 | Rubbert et al. | |
| 2002/0015934 A1 | 2/2002 | Rubbert et al. | |
| 2003/0194677 A1 | 10/2003 | Sachdeva et al. | |
| 2004/0175670 A1 | 9/2004 | Kopelman et al. | |
| 2005/0208450 A1 | 9/2005 | Sachdeva et al. | |

FOREIGN PATENT DOCUMENTS

| | | |
|---|---|---|
| EP | 0299490 A2 | 1/1989 |
| EP | 0376873 A2 | 7/1990 |
| EP | 0490848 A2 | 6/1992 |
| EP | 0774933 B1 | 5/1997 |
| EP | 0541500 A1 | 6/1998 |
| EP | 0731673 B1 | 9/1998 |
| FR | 2369828 A1 | 6/1978 |
| FR | 2652256 A1 | 3/1991 |
| WO | WO90/08512 A1 | 8/1990 |
| WO | WO91/04713 A1 | 4/1991 |
| WO | WO94/10935 A1 | 5/1994 |
| WO | WO98/44865 A1 | 10/1998 |
| WO | WO98/58596 A1 | 12/1998 |

OTHER PUBLICATIONS

Orametrix, Inc., "The SureSmile White Paper, SureSmile and Straight-Wire, Correcting for Limitation in the Straight Archwire Approach"(Dec. 10, 2002) pp. 1-5.

Alexander et al., "The DigiGraph Work Station Part 2, Clinical Management," *JCO* (Jul. 1990), pp. 402-407.

Altschuler et al, "Measuring Surfaces Space-Coded by a Laser-Projected Dot Matrix," *SPIE Imaging Applications for Automated Industrial Inspection and Assembly*, vol. 182 (1979), p. 187-191.

Altschuler et al., "Analysis of 3-D Data for Comparative 3-D Serial Growth Pattern Studies of Oral-Facial Structures," IADR Abstracts, Program and Abstracts of Papers, 57th General Session, IADR Annual Session, Mar. 29, 1979 - April 1, 1979, New Orleans Marriot, *Journal of Dental Research*, vol. 58, Jan. 1979, Special Issue A, p. 221.

Altschuler et al., "Laser Electro-Optic System for Rapid Three-Dimensional (3D) Topographic Mapping of Surfaces," *Optical Engineering*, vol. 20(6) (1981), pp. 953-961.

Altschuler, "3D Mapping of Maxillo-Facial Prosthesis," AADR Abstract #607, 1980, 1 page total. .

American Association for Dental Research, Summary of Activities, Mar. 20-23, 1980, Los Angeles, CA, p. 195.

Andersson et al., "Clinical Results with Titanium Crowns Fabricated with Machine Duplication and Spark Erosion,"*Acte Odontological Scandinavia*, vol. 47 (1989), pp. 279-286.

Baumrind et al., "A Stereophotogrammetric System for the Detection of Prosthesis Loosening in Total Hip Anthroplasty", NATO Symposium on Applications of Human Biostereometrics, Jul. 9-13, 1978, SPIE vol. 166, pp. 112-123.

Baumrind et al., Mapping the Skull in 3-D, Reprinted from The Journal, *California Dental Association*, vol. 48, No. 2 (1972 Fall Issue) 11 pages total.

Baumrind, "A System for Craniofacial Mapping Through the Integration of Data from Stereo X-Ray Films and Stereo Photographs," An invited paper submitted to the 1975 American Society of Photogram. Symposium on Close-Range Photogram. Systems, University of Ill., Aug. 26-30, 1975, pp. pp. 142-166.

Baumrind, "Integrated Three-Dimensional Craniofacial Mapping: Background, Principles, and Perspectives," *Seminars in Orthodontics*, vol. 7, No. 4 (Dec. 2001), pp. 223-232.

Begole et al., "A Computer System for the Analysis of Dental Casts," *The Angle Orthodontist*, vol. 51 No. 3 (Jul. 1981), pp. 253-259.

Bernard et al., "Computerized Diagnosis in Orthodontics for Epidemiological Studies: A Progress Report", Abstracts of Papers, *Journal of Dental Research*; vol. 67, Special Issue Mar. 9-13, 1988, p. 169.

Bhatia et al., "A Computer-Aided Design for Orthognathic Surgery," *British Journal of Oral and Maxillofacial Surgery*, vol. 22 (1984), pp. 237-253.

Biggerstaff et al., "Computerized Analysis of Occlusion in The Postcanine Dentition," *American Journal of Orthodontics*, vol. 61, No. 3 (Mar. 1972), pp. 245-254.

Biggerstaff, "Computerized Diagnostic Setups and Simulations," *The Angle Orthodontist*, vol. 40, No. 1 (Jan. 1970), pp. 28-36.

Boyd et al., "Three Dimensional Diagnosis and Orthodontic Treatment of Complex Malocclusions With the Invisalign Appliance", *Seminars in Orthodontics*, vol. 7, No. 4 (Dec. 2001), p. 274-293.

Brandestini et al., "Computer Machined Ceramic Inlays: In Vitro Marginal Adaptation," *Journal of Dental Research*, vol. 64/Special Issue/Abstracts, IADR/AADR Abstracts 1985, p. 208.

Brook et al., An Image Analysis System for the Determination of Tooth Dimensions from Study Casts: Comparison with Manual Measurements of Mesio-distal Diameter, *J Dent Res.*, vol. 65, No. 3, Mar. 1986, pp. 428-431.

Burstone (interview), "Dr. Charles J. Burstone on The Uses of the Computer in Orthodontic Practice (Parts1 and 2)," *Journal of Clinical Orthodontics*, (Part 1) vol. 8, No. 7 , July 1979; (Part 2) vol. 8, No. 8 pp. 539-551, Aug. 1979.

Burstone et al., "Precision Adjustment of the Transpalatal Lingual Arch: Computer Arch Form Predetermination," *Am. Journal of Orthodontics*, vol. 79, No. 2 (Feb. 1981), pp. 115-133.

Chaconas et al., "The DigiGraph Work Station, Part 1, Basic Concepts," *JCO*(Jun. 1990), pp. 360-367.

Chafetz et al., "Subsidence of the Femoral Prothesis, A Stereophotogrammetric Evaluation," *Clinical Orthopaedics and Related Research*, No. 201 (Dec. 1985), pp. 60-67.

Chiappone, "Constructing the Gnathologic Setup And Positioner" *J. Clin. Orthod.*, 14:121-133, 1980.

Cottingham, "Gnathologic Clear Plastic Positioner" *Am. J. Orthod.*, vol. 55, No. 1, (Jan. 1969),. pp. 23-31.

Crawford, "Computers in Dentistry: Part 1: CAD/CAM: The Computer Moves Chairside,"0 "Part 2: F. Duret—A Man With A Vision," "Part 3: The Computer Gives New Vision—Literally, " "Part 4: Bytes 'N Bites" The Computer Moves From The Front Desk To The Operatory, *Canadian Dental Journal*, vol. 54(9), , (1988), pp. 661-666.

Crawford, "CAD/CAM in the Dental Office: Does It Work?" *Canadian Dental Journal*, vol. 57, No. 2 (Feb. 1991), pp. 121-123.

Crooks, "CAD/CAM Comes to USC," *USC Dentistry*, (Spring 1990) pp. 14-17.

Cureton, "Correcting Malaligned Mandibular Incisors With Removable Retainers" *J. Clin. Orthod.*, 30:390-395, 1996.

Curry et al., "Integrated Three-Dimensional Craniofacial Mapping at the Craniofacial Research Instrumentation Laboratory/University of the Pacific," *Seminars in Orthodontics*, vol. 7, No. 4 (Dec. 2001), pp. 258-265.

Cutting et al., "Three-Dimensional Computer-Assisted Design of Craniofacial Surgical Procedures: Optimization and Interaction with Cephalometric and CT-Based Models," *Plastic and Reconstructive Surgery*, vol. 77, No. 6 (Jun. 1986), pp. 877-885.

DCS Dental AG, "The CAD/CAM 'DCS Titan System' for Production of Crowns/Bridges" *DSC Production AG*, Jan. 1992, pp. 1-7.

Defranco et al., "Three-Dimensional Large Displacement Analysis of Orthodontic Appliances," *J. Biomechanics*, vol. 9 (1976), pp. 793-801.

Dental Institute University of Zurich Switzerland, Program for International Symposium on Computer Restorations: State of the Art of the CEREC-Method, May 1991, 2 pages total.

DenTrac Corporation, Dentrac document, pp. 4-13.

Duret et al, "CAD-CAM in Dentistry," *Journal of the American Dental Association*, vol. 117 (Nov. 1988), pp. 715-720.

Duret et al., "CAD/CAM Imaging in Dentistry," *Current Opinion in Dentistry*, vol. 1 (1991), pp. 150-154.

Duret, "Vers une prosthese informatisee," (English translation also attached), *Tonus*, vol. 75, (Nov. 15, 1985), pp. 55-57.

Duret, "The Dental CAD/CAM, General Description of the Project," *Hennson International Product Brochure*, Jan. 1986., 18 pages total.

Economides, "The Microcomputer in the Orthodontic Office," *JCO*, (Nov. 1979), pp. 767-772.

Elsasser, "Some Observations on the History and Uses of the Kesling Positioner" *Am. J. Orthod.*, vol. 36, No. 5, (May1950) pp. 368-374.

Faber et al., "Computerized interactive orthodontic treatment planning," *Am. J. Orthod.*, vol. 73, No. 1 (Jan. 1978), pp. 36-46.

Felton et al. "A computerized analysis of the shape and stability of mandibular arch form," *Am. Journal of Orthodontics and Dentofacial Orthopedics*, vol. 92, No. 6 (Dec. 1987), pp. 478-483.

Friede et al., "Accuracy of Cephalometric Prediction in Orthognathic Surgery," Abstract of Papers, *Journal of Dental Research*, vol. 70 (1987), pp. 754-760.

Gim-Alldent Deutschland, "Das DUX System: Die Technik" 2 pages total.

Grayson, "New Methods for Three Dimensional Analysis of Craniofacial Deformity," Symposium: Computerized Facial Imaging in Oral and Maxilofacial Surgery Presented on Sep. 13, 1990, AAOMS 72nd Annual Meeting and Scientific Sessions, Sep. 13, 1990, New Orleans, *Journal of Oral and Maxillofacial Surgery*, vol. 48, No. 8, Supp. 1, Aug. 1990, p. 5-6.

Guess et al., "Computer Treatment Estimates in Orthodontics and Orthognathic Surgery," *JCO*, (Apr. 1989), pp. 262-228.

Heaven et al., "Computer-based Image Analysis of Artificial Root Surface Caries," Abstracts of Papers, *Journal of Dental Research*, vol. 70,Apr. 17-21, 1991, p. 528.

Hoffmann et al., "Role of Cephalometry for Planning of Jaw Orthopedics and Jaw Surgery Procedures," (Article Summary in English, article in German). *Informationen*, (Mar. 1991), pp. 375-396.

Huckins, "CAD-CAM Generated Mandibular Model Prototype from MRI Data," *AAOMS*, 1999, p. 96.

JCO Interviews, "Craig Andreiko , DDS, MS on the Elan and Orthos Systems", JCO, (Aug. 1994), pp. 459-468.

JCO Interviews, "Dr. Homer W. Phillips on Computers in Orthodontic Practice, Part 2," JCO, (Dec. 1983), pp. 819-831.

Jerrold, "The Problem, Electronic Data Transmission and the Law," *AJO-DO*, (Apr. 1988), pp. 478-479.

Jones et al., "An Assessment of the Fit of a Parabolic Curve to pre- and Post-Treatment Dental Arches," *British Journal of Orthodontics*, vol. 16 (1989), pp. 85-93.

Kamada et al., "Case Reports on Tooth Positioners Using LTV Vinyl Silicone Rubber" J. Nihon University School of Dentistry, 26(1):11-29, 1984.

Kamada et al., "Construction of Tooth Positioners With LTV Vinyl Silicone Rubber and Some Case Reports" J. Nihon University School of Dentistry, 24(1):1-27, 1982.

Kanazawa et al., "Three-Dimensional Measurements of the Occlusal Surfaces of Upper Molars in a Dutch Population," *J. Dent. Res.*, vol. 63, No. 11 (Nov. 1984), pp. 1298-1301.

Kesling, "Coordinating the Predetermined Pattern and Tooth Positioner With Conventional Treatment" *Am. J. Orthod. Oral. Surg.*, 32:285-293, 1946.

Kesling, "The Philosophy of the Tooth Positioning Appliance" *Am. J. Orthod. Oral. Surg.*, 31(6):297-304, 1945.

Kleemann et al., "The Speed Positioner" *J. Clin. Orthod.*, 30:673-680, 1996.

Kuroda et al., "Three-dimensional dental cast analyzing system using laser scanning" *Am. J. Orthod. Dentofac. Orthop.*, 110:365-369, 1996.

Laurendeau et al., "A Computer-Vision Technique for the Acquisition and Processing of 3-D Profiles of Dental Imprints: An Application in Orthodontics," *IEEE Transactions on Medical Imaging*, vol. 10, No. 3 (Sep. 1991), pp. 453-461.

Leinfelder et al., "A new method for generating ceramic restorations: a CAD-CAM system," *Journal Of The American Dental Assoc.*, vol. 118, No. 6 (Jun. 1989), pp. 703-707.

Manetti et al., "Computer-aided Cefalometry and New Mechanics in Orthodontics" (Article Summary in English, article in German), *Fortschr. Kieferorthop*, 44, 370-376 (Nr. 5), 1983.

McCann, Inside the ADA, *Journal Of The American Dental Assoc.*, vol. 118 (Mar. 1989) pp. 286-294.

McNamara et al., "Invisible Retainers", *J. Clinical Orthodontics*, (Aug. 1985) pp. 570-578.

McNamara et al., Chapter 19: Invisible Retainers, *Orthodontic and Orthopedic Treatment in the Mixed Dentition*, Needham Press, Jan. 1993, pp.347-353.

Moermann et al., "Computer Machined Adhesive Porcelain Inlays: Margin Adaptation after Fatigue Stress," IADR Abstract 339, *Journal of Dental Research*, vol. 66(a) (1987), p. 763.

Mörmann et al., "Marginal Adaptation von adhasiven Porzellaninlays in vitro," *Schwizerische Monatsshrift fur zahnmedizin*, vol. 85 (1985), p. 1118-1129.

Nahoum, "The Vacuum Formed Dental Contour Appliance" *The New York State Dental Journa*, 30(9):385-390, Nov. 1964.

Nash, "CEREC CAD/CAM Inlays: Aesthetics and Durability in a Single Appointment," *Dentistry Today*, (Oct. 1990), pp. 20, 22-23, 54.

Nishiyama et al., "A New Construction Of Tooth Repositioner By LTV Vinyl Silicone Rubber" J. Nihon University School of Dentistry, 19(2):93-102, 1977.

Pinkham, "Foolish Concept Propels Technology," *Dentist*, Jan./Feb. 1989, 3 pages total.

Pinkham, "Inventor's CAD/CAM May Transform Dentistry," *Dentist*, Sep. 1990, 3 pages total.

Ponitz, "Invisible Retainers", *Am. J. Orthodontics*, vol. 59, No. 3, Mar. 1971, pp. 266-272.

Procera Research Projects, *PROCERA Research Projects*1993-Abstract Collection, 1993, pp. 3-24.

Rekow, "A Review of the Developments in Dental CAD/CAM Systems," (contains references to Japanese efforts and content of the papers of particular interest to the clinician are indicated with a one-line summary of their content in the bibliography), Dental Clinics: *Prosthodontics and Endodontics*, pp.25-33, 1992.

Rekow, "CAD/CAM in Dentistry: A Historical Perspective and View of the Future," *Journal*vol. 58 No. 4, (Apr. 1992), pp. 283, 287-288.

Rekow, "Computer-Aided Design and Manufacturing in Dentistry: A Review of the State of the Art," *The Journal of Prosthetic Dentistry*, vol. 58, No. 4 (Oct. 1987), pp. 512-516.

Rekow, "Dental CAD-CAM Systems: What is the State of the Art?" *Journal of the American Dental Assoc.*, vol. 122 (1991), pp. 43-48.

Rekow, Feasibility of an Automated System for Production of "Dental Restorations," PhD Thesis, Univ. of Minnesota, Nov. 1988, 244 pages total.

Richmond et al., Research Reports, "The Development of a 3D Cast Analysis System," *British Journal of Orthodontics*, vol. 13, No. 1, (Jan. 1986) pp. 53-54.

Richmond, "Recording The Dental Cast in Three Dimensions," *Am. J. Orthod. Dentofac. Orthop.*, vol. 92, No. 3, (Sep. 1987), pp. 199-206.

Rudge, "Dental arch analysis: Arch Form, A review of the literature," *European Journal of Orthodontics*, vol. 3, No. 4(1981), pp. 279-284.

Sakuda et al., "Integrated information-processing system in clinical orthodontics: An approach with use of a computer network system," *Am. J. Orthod. Dentofac. Orthop.*vol. 101 No. 3 (Mar. 1992), pp. 210-220.

Schellhas et al., "Three-Dimensional Computed Tomography in Maxillofacial Surgical Planning," *Arch Otolamgol Head Neck Surg.* vol. 114 (Apr. 1988), pp. 438-442.

Shilliday, "Minimizing Finishing Problems With the Mini-Positioner" *Am. J. Orthod.*59:596-599, 1971.

Siemens, "CEREC—Computer-Reconstruction," High Tech in der Zahnmedizin, 14 page total.

Sirona Dental Systems GmbH, CEREC 3D, Manuel utilisateur, Version 2.0X (in French), 2003, 114 pages total.

Stoll et al., "Computer-aided Technologies in Dentistry" (Article Summary in English, article in German), *Dtsch ZahnārztlZ* 45, 314-322, 1990.

U.S. Department of Commerce, National Technical Information Service, "Automated Crown Replication Using Solid Photography SM," Solid Photography Inc. Melville NY, Oct. 1977, 20 pages total.

U.S. Department of Commerce, National Technical Information Service, "Holodontography: An Introduction to Dental Laser Holography," School of Aerospace Medicine Brooks AFB Tex, Mar. 1973, 37 pages total.

U.S. Provisional Patent Appl. No. 60/050342, filed on Jun. 20, 1997, 41 pages total.

Van Der Linden et al., "Three-Dimensional Analysis of Dental Casts by Means of the Optocom," *J Dent Res*, Jul.-Aug. 1972, vol. 51, No. 4, p. 1101.

Van Der Linden, "A New Method to Determine Tooth Positions and Dental Arch Dimensions," Jul.-Aug. 1972, p. 1104.

Van Der Zel, "Ceramic-fused-to-metal Restorations with a New CAD/CAM System," *Quintessence International*, vol. 24(11) (1993), pp. 769-778.

Varady et al., Reverse Engineering Of Geometric Models-An Introduction. Computer-Aided Design, 29(4):255-268, 1997.

Warunek et al., "Clinical Use Of Silicone Elastomer Appliances" *JCO*, MH (10):694-700, 1989.

Warunek et al., "Physical And Mechanical Properties of Elastomers In Orthodontic Positioners"*Am. J. Orthod. Dentofac. Orthop.*, 95:388-400, 1989.

Wells, "Application of the Positioner Appliance in Orthodontic Treatment" *Am. J. Orthodont.*, 58:351-366, 1970.

Williams, "Dentistry and CAD/CAM: Another French Revolution," *Journal of Dental Practice Admin.*, Jan./Mar. 1987, pp. 2-5.

Williams, "The Switzerland and Minnesota Developments in CAD/CAM," *Journal of Dental Practice Admin.*, pp. 50-55, Apr./Jun. 1987.

Wishan, "New Advances in Personal Computer Applications for Cephalometric Analysis, Growth Prediction, Surgical Treatment Planning and Imaging Processing," Symposium: Computerized Facial Imaging in Oral and Maxillofacial Surgery Presented on Sep. 13, 1990, AAOMS 72nd Annual Meeting and Scientific Sessions, Sep. 13, 1990, New Orleans, *Journal of Oral and Maxillofacial Surgery*, vol. 48, No. 8, Supp. 1, Aug. 1990, p. 5.

Yamamoto et al., "Three-Dimensional Measurement of Dental Cast Profiles and Its Applications to Orthodontics," Annual Int'l Conf. of IEEE Engineering in Medicine and Biology Society, vol. 12, No. 5, pp. 2051-2053, 1990.

Yamamoto et al., "Optical Measurement of Dental Cast Profile and Application to Analysis of Three-Dimensional Tooth Movement in Orthodontics," *Frontiers in Med. and Biol. Eng'g*, vol. 1, No. 2 (1988), pp. 119-130.

* cited by examiner

SYSTEM AND METHODS FOR COMBINATION TREATMENTS OF DENTAL PATIENTS

CROSS-REFERENCE TO RELATED APPLICATIONS

The present application is a continuation of application Ser. No. 10/375,224, filed Feb. 26, 2003 abandoned, the full disclosure of which is incorporated herein by reference.

BACKGROUND

The present invention relates generally to the field of orthodontics.

One objective in orthodontics is to move a patient's teeth to a position where the teeth function optimally and are also aesthetically pleasing. Conventional appliances such as braces and wires can be positioned on a patient's teeth by a treatment provider such as an orthodontist or a suitably trained dentist. Once mounted on the teeth, the hardware exerts continual forces on the teeth and gradually urges the teeth toward their ideal positions. Over a period of time, the treatment provider adjusts the braces and the wires to move the teeth toward their final destination.

Orthodontic brackets are often bonded directly to the patient's teeth. Typically, a small quantity of adhesive is placed on the base of each bracket and the bracket is then placed on a selected tooth. Before the adhesive is set, the bracket is maneuvered to a desired location on the tooth. Once the adhesive has hardened, the bracket is bonded to the tooth with sufficient strength to withstand subsequent orthodontic forces as treatment progresses. One shortcoming with this technique is the difficulty in accessing the optimal surface for bracket placement on severely crowded teeth or in teeth where the bonding surface is obstructed by teeth in the opposing arch during jaw closure. With posterior teeth, the treatment provider may have difficulty seeing the precise position of the bracket relative to the tooth surface. The amount of time needed to carry out the bonding procedure may be a nuisance both to the patient as well as to the treatment provider. Also, the necessity of minimizing moisture contamination from the patient's saliva can prolong the procedure and also unduly impair the accuracy of placement of the brackets on the teeth. All of these factors increase the chance that the ultimate adhesive bond will not have sufficient strength to retain the brackets on the teeth during treatment. One way to overcome some of the limitations of direct bracket placement is with indirect bonding. Typically, an impression of each of the patient's dental arches is taken and a replica plaster or "stone" model is made from each impression and sealed. Brackets are bonded to the sealed stone models using a temporary cement. A transfer tray is then made by placing matrix material over both the model and the brackets on the model. For example, a heated plastic sheet matrix material may be placed over the model and brackets and then under pressure. The plastic sheet material then assumes a configuration that precisely matches the shape of the replica teeth of the stone model with the brackets in the desired position. The plastic material is then allowed to cool and harden to form a tray. The temporary adhesive is removed, and permanent adhesive is placed on the base of each bracket in the tray, and the tray with the embedded brackets then placed over matching portions of the patient's dental arches. Since the configuration of the interior surface of the tray closely matches the respective portions of the patient's dental arches, each bracket is ultimately positioned on the patient's teeth at precisely the same location that corresponds to the previous location of the same bracket on the stone model. The adhesive is hardened and the matrix material removed, leaving the brackets in the desired positions. This method however, is labor intensive. An additional problem with the indirect method is that brackets may become dislodged during the removal of the matrix from the dental arches. The problem of proper access to tooth surfaces for optimal placement in the event of severely crooked teeth or teeth which interfere with the opposing arch such that brackets cannot be placed is also not addressed.

New methods such as those described in U.S. Pat. No. 5,975,893, commonly assigned to the assignee of the instant invention, allow the treatment to be planned in advance and a plurality of polymeric shell appliances are fabricated at the outset of treatment. The use of polymeric shell appliances provides treatments that are more comfortable; less visible, and removable by the patient, and greatly improves patient compliance, comfort, and satisfaction.

Since each patient is unique and requires customized treatment, on occasion, a patient may need to utilize a combination of braces/wires and shell appliances. Ideally, a device would enable precise placement of brackets on teeth with minimal risk of displacing the brackets upon removal of the matrix and allow final placement to be independent of adjacent geometries. In other words, placement of obscured tooth surfaces may be accomplished at a later time when the tooth surfaces have been exposed through initial uncrowding of severely overlapped teeth.

SUMMARY

Systems and methods for fabricating a dental template to position an object on a patient's tooth to move the tooth from an initial position to a target position are disclosed. The system digitizes a model of the patient's tooth at the initial position; places an object on the tooth model at the target position; determines the position of the object at the initial position; and fabricates the dental template to locate the object on the patient's tooth.

In another aspect, a method to position a bracket on a patient's tooth includes digitizing the patient's tooth at an initial tooth position; determining a final position for the tooth; placing the bracket on the final tooth position; determining the position of the bracket on the initial tooth position based on the bracket position on the final tooth position; and fabricating a dental appliance to mount the bracket on the patient's tooth.

Implementations of the above aspects may include one or more of the following. The object can be a bracket and the bracket is positioned in its slot to receive an orthodontic wire. The method includes positioning a plurality of brackets on the patient's teeth at the target position, each bracket having a slot adapted to receive an orthodontic wire passing therethrough; and aligning the brackets to minimize strain on the wire at the target position. The wire at the target position is arch-shaped and wherein the wire at the initial position is irregular. The method includes interactively adjusting the position of the object. The method also includes determining a deviation of the object from an ideal placement and iteratively adjusting the position of the object to minimize the deviation. The fabricating includes rendering a physical dental template using a rapid prototyping method. The object can be embedded in the dental template or can be inserted into an opening on the dental template prior to being bonded on the tooth. The wire at the target position is arch-shaped, while the wire at the initial position is irregular. The template is articulable with a plurality of flexibly linked cavities. The template can be used for treating teeth using a combination of removable and fixed appliances. The fixed appliance covers two or more teeth on an arch (portion of arch) or the entire arch. The fixed appliance can also be positioned on a lingual side of the patient's teeth.

In yet another aspect, an apparatus to fabricate a dental template to position an object on a patient's tooth to move the tooth from an initial position to a target position includes a scanner to digitize a model of the patient's tooth at the initial position; means for placing an object on the tooth model at the target position; means for determining the position of the object at the initial position; and a machine to fabricate the dental template to locate the object on the patient's tooth.

Implementations of the above aspect may include one or more of the following. The machine can be a rapid prototyping machine. The apparatus can include means for determining a deviation of the object from an ideal placement and iteratively adjusting the position of the object to minimize the deviation.

Advantages of the template may include one or more of the following. The template can be used for etching or for positioning brackets on teeth. The treatment can be done virtually and the placement of the brackets can be done using a template device that is a removable guide. This device allows precise placement of the bracket and enables bracket placement onto specific teeth independent of overall arch geometry. The template makes it easier for a less well-trained or an untrained person to bond a bracket. The system minimizes variations in the perception of distance and angles. The template provides a very precise control on the placement of the bracket. Since bracket placement is one of the critical variables to successful treatment, the template improves treatment precision from patient to patient and from tooth to tooth.

The device itself may not necessarily contain the bracket as with traditional indirect bonding (IDB) templates, but rather, directs the user as to the precise location where the bracket should be placed based on geometric fit.

DESCRIPTION

Figure 1:
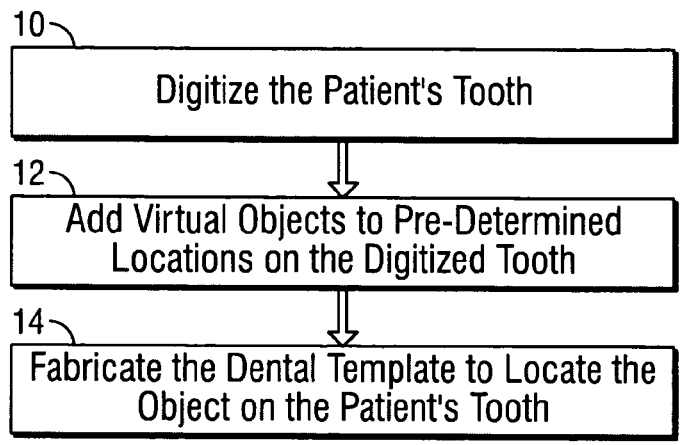
FIG. 1 shows an exemplary method or process to fabricate a dental template to position an object on a patient's tooth.

FIG. 1 shows an exemplary method or process to fabricate a dental template to position an object on a patient's tooth. First, the process digitizes the patient's tooth (10). Next, virtual objects are added to pre-determined locations on the digitized tooth (12). Finally, the process fabricates the dental template to locate the object on the patient's tooth (14). One detailed implementation of FIG. 1 is described in FIGS. 3A and 3B below.

Figure 2A:
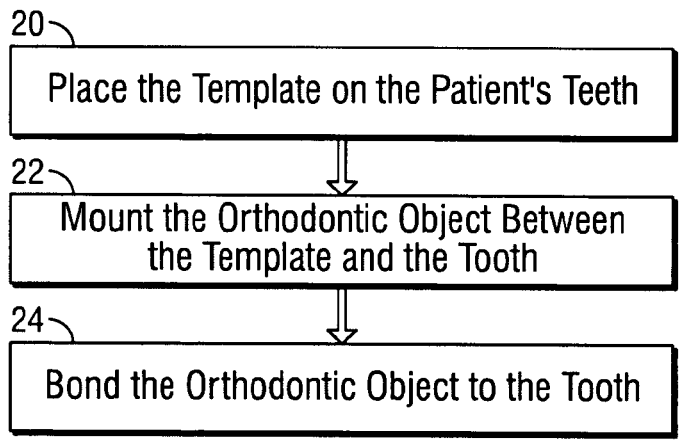
FIG. 2A shows an exemplary method or process for placing an orthodontic object on a patient's tooth.

FIG. 2A shows an exemplary method or process for placing an orthodontic object on a patient's tooth. The process uses the template fabricated in the process of FIG. 1. The process includes placing the template on the patient's teeth (20); mounting the orthodontic object between the template and the tooth (22); and bonding the orthodontic object to the tooth (24). In the bonding operation, chemical curing or light curing adhesives can be used. In chemical curing, separately supplied curing components are mixed together and a small quantity of the mixture is placed on the back of the bracket prior to placing the bracket on the tooth. Light-curable adhesives include a photo-initiator that initiates the curing reaction once the adhesive is exposed to a sufficient amount of light. A common method of using light-curable adhesives for direct bonding includes the steps of placing a small quantity of the adhesive on the base of the bracket and then placing the bracket on the patient's tooth. The practitioner then shifts the bracket on the tooth as may be needed. Once the bracket is in its precise, intended location, light from a dental curing unit is directed toward the adhesive for a time period sufficient to satisfactorily cure the adhesive.

Figure 2B:
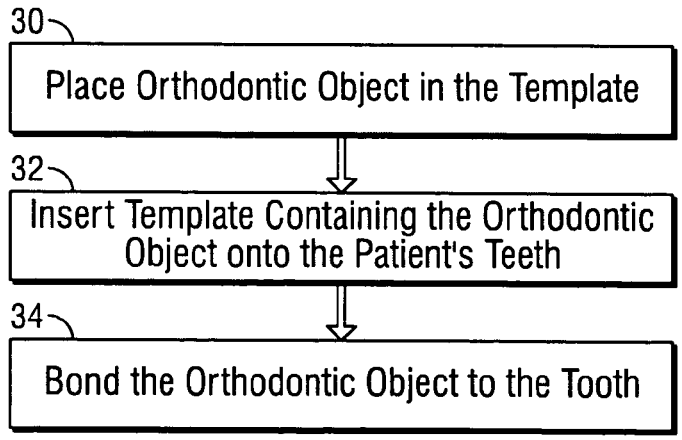
FIG. 2B shows a second method of placing the orthodontic object on a patient's tooth.

FIG. 2B shows a second method of placing the orthodontic object on a patient's tooth. In this process, the orthodontic object is placed in the template (30). Next, the process includes inserting the template containing the orthodontic object onto the patient's teeth (32). Finally, the process includes bonding the orthodontic object to the tooth (34).

Figure 3A:
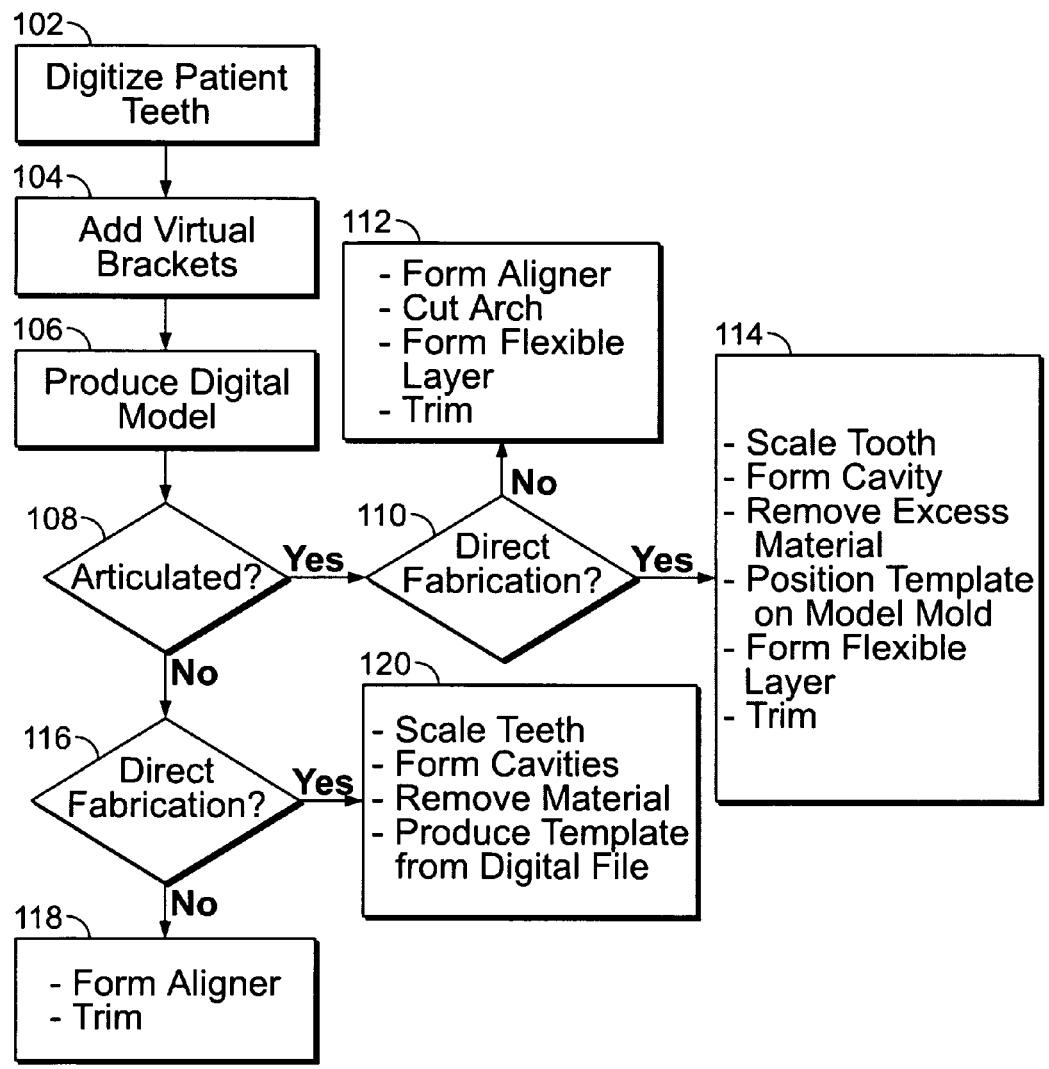
FIG. 3A illustrates an exemplary process for fabricating the dental template.

FIG. 3A illustrates an exemplary process for fabricating the dental template. First, a digital model of a patient's teeth of a patient is obtained (102). The digital model can be obtained in a variety of ways. For example, the patient's teeth may be scanned or imaged using well known technology, such as X-rays, three-dimensional x-rays, computer-aided tomographic images or data sets, magnetic resonance images, etc. There are a variety of range acquisition systems, generally categorized by whether the process of acquisition requires contact with the three dimensional object. A contact-type range acquisition system utilizes a probe, having multiple degrees of translational and/or rotational freedom. By recording the physical displacement of the probe as it is drawn across the sample surface, a computer-readable representation of the sample object is made. A non-contact-type range acquisition device can be either a reflective-type or transmissive-type system. There are a variety of reflective systems in use. Some of these reflective systems utilize non-optical incident energy sources such as microwave radar or sonar. Others utilize optical energy. Those non-contact-type systems working by reflected optical energy further contain special instrumentation configured to permit certain measuring techniques to be performed (e.g., imaging radar, triangulation and interferometry).

Next, virtual brackets are selected (104). The virtual brackets are 3D models of existing brackets. The 3D models may be a computer aided design (CAD) model or may be scanned using scanners described above. The brackets may be positioned on a digitized tooth using a computer or workstation having a suitable graphical user interface (GUI) and software appropriate for viewing and modifying the images. The above-described component identification and component manipulation software is designed to operate at sophistication commensurate with the operator's training level. For example, the component manipulation software can assist a computer operator, lacking orthodontic training, by providing feedback regarding permissible and forbidden manipulations of the teeth. On the other hand, an orthodontist, having greater skill in intra-oral physiology and teeth-moving dynamics, can simply use the component identification and manipulation software as a tool and disable or otherwise ignore the advice.

While the methods will rely on computer manipulation of digital data, the dental templates or appliance may be produced by non-computer-aided techniques. For example, plaster casts obtained as described above may be cut using knives, saws, or other cutting tools in order to permit repositioning of individual teeth within the casting. The disconnected teeth may then be held in place by soft wax or other malleable material, and a plurality of intermediate tooth arrangements can then be prepared using such a modified plaster casting of the patient's teeth. The different arrangements can be used to prepare the template using pressure and vacuum molding techniques. While such manual creation of the appliance systems of the present invention will generally be much less preferred, systems so produced will come within the scope of the present invention.

Using the CAD workstation, a combined digital model of the virtual brackets and the teeth is produced (106).

In one implementation, one of four template embodiments can be selected: Direct-Articulated, Indirect-Articulated, Direct-Unified, and Indirect-Unified, as discussed in more detail in FIG. 3B.

Once the template has been fabricated, in one embodiment, the system sets the template over the model of the patient's arches or otherwise positions the template in the approximate locations of their respective teeth. A thermoformed, cast, or otherwise formed layer of flexible material is deposited on the bodies. The layer makes intimate and relatively durable contact with the bodies of the templates. This may be accomplished, among other ways, by adding or subtracting geometries to the bodies to engage well with the material layer. This method could be performed either by a factory or in the orthodontist's office.

The system produces both the template bodies and the inter-tooth portion(s) at the same time and subsequently alter the stiffness of the various parts. One way of achieving this would be to produce the entire arch with a 3-D printer, mask the tooth bodies from the inter-tooth portions, and embed the tooth bodies with a rigidifying agent and the inter-tooth portions with an agent to create flexibility.

From 108, if an articulated template is to be produced, the process proceeds to 110 where, if a directly formed template is produced, the process proceeds to 114 where each tooth is scaled; a cavity is formed to enclose the tooth when the dental template or appliance is inserted over the patient's teeth. Next, unnecessary structures are removed from the digital model. The digital model is produced as a physical model. A flexible pliable layer is formed and the resulting combination is trimmed to allow proper fit and function.

Alternatively, from 110 if indirect forming is to be done, the process forms an aligner, and cuts and removes excess material (112).

From 108, if a non-articulated template is to be indirectly fabricated (116), an aligner is formed and trimmed (118). In the case of a directly formed non-articulated template (116), the process proceeds to 120 where each tooth in the arch is scaled; cavities are formed to enclose the teeth when the dental template or appliance is inserted over the patient's teeth. Next, unnecessary structures are removed from the digital model. The digital model is produced as a physical model.

Figure 3B:
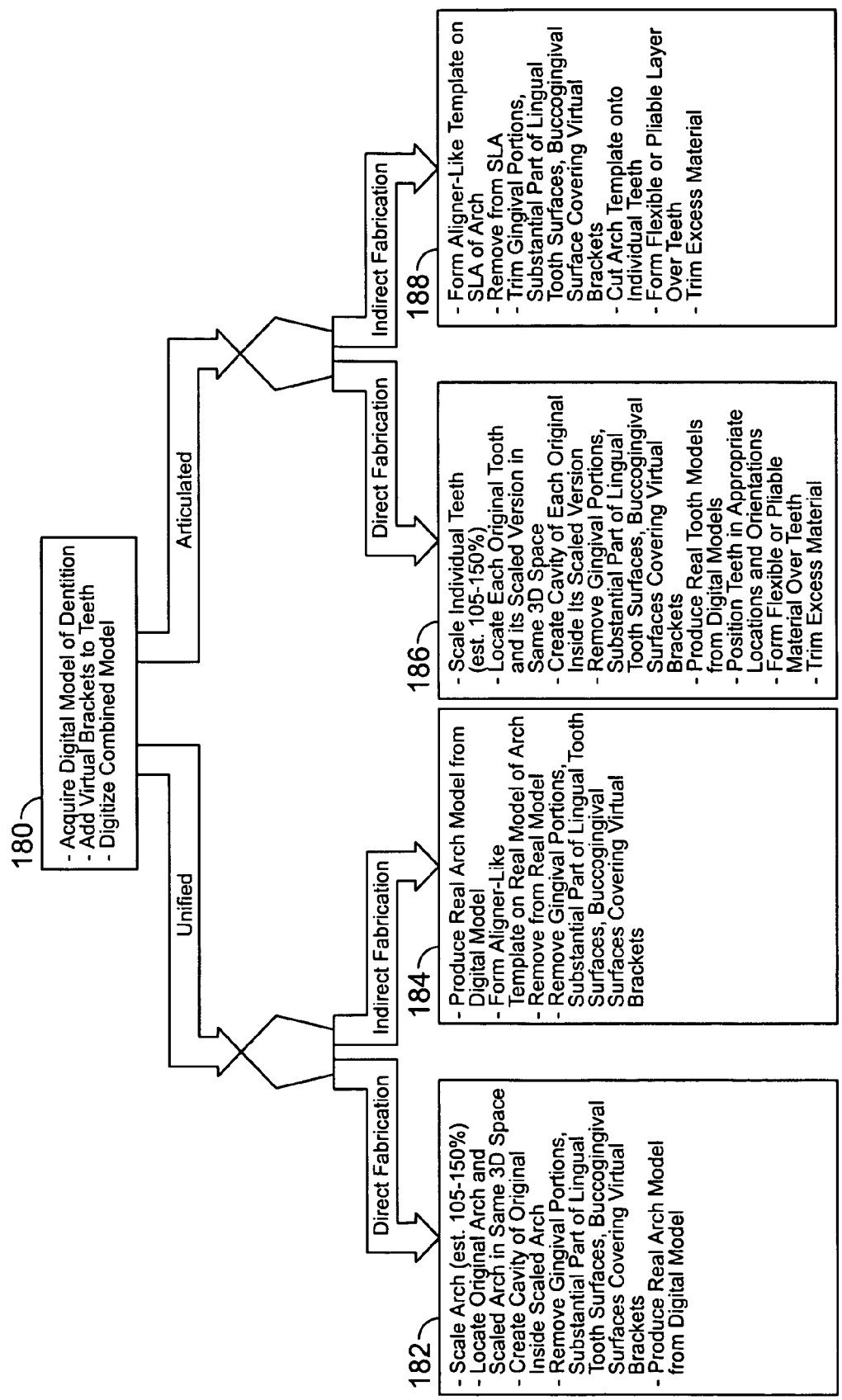
FIG. 3B shows a process for providing four possible templates.

FIG. 3B shows a process for providing four possible templates. First, the process acquires a digital model of dentition, adds virtual brackets to teeth, and creates a combined model (180). Next, one of four templates options can be selected. The first option is unified (or single piece)—direct fabrication option where the process scales the arch (est. 105–150%), locates original arch and scaled arch in same 3D space, creates cavity of original inside scaled arch, removes gingival portions, substantial part of lingual tooth surfaces, buccogingival surfaces covering virtual brackets, and produces real arch model from digital model (182).

In the second option (unified indirect fabrication), the process produces real arch model from digital model and forms a removable appliance (aligner) template on real model of arch. The template is removed from the real model, and the process then removes gingival portions, substantial part of lingual tooth surfaces, buccogingival surfaces covering virtual brackets (184).

In the third option (articulated direct fabrication), the process scales individual tooth (est. 105–150%), locates each original tooth and its scaled version in same 3D space, creates a cavity of each original inside its scaled version, removes gingival portions, substantial part of lingual tooth surfaces, buccogingival surfaces covering virtual brackets, produces real tooth models from digital models, positions teeth in appropriate locations and orientations, forms a flexible or pliable material over teeth, and trims excess material from the template (186).

In the fourth option (articulated indirect fabrication), the process forms an aligner-like template on a mold of an arch. The template is removed from the mold and gingival portions, substantial part of lingual tooth surfaces, and buccogingival surface covering virtual brackets are trimmed. The process cuts an arch template onto an individual tooth. A flexible or pliable layer over the template is formed, and excess material is trimmed (188).

In yet another embodiment, a process obtains tooth geometries. If direct fabrication is to be used, the process performs the following:

- Scale the teeth to values likely within the range 105–150%.
- Co-locate the original (100%) teeth and the scaled teeth in the same 3D space
- Place a virtual bracket or other appropriate geometry at a specific location and in a specific orientation on each tooth to be treated.
- Cavity the original teeth and the brackets in the scaled teeth.
- Remove from the resulting template or body those aspects that would be below the gingival line. Remove the portions of the resultant body buccal and gingival to the brackets remove a substantial portion or all of the lingual aspect of the resultant body.
- Convert this computer model to a real part, likely through the use of a rapid prototyping method (e.g. Fused Deposition Modeling, 3-D Printing, and stereolithography).

If indirect fabrication is to be done, the following operations are done using an arch model:

- Form an Aligner-like appliance or template over an arch model that has brackets or other appropriate geometries properly located on the teeth.
- Remove from the Aligner or template those aspects that would be below the gingival line or in direct interproximal contact with adjacent teeth. Remove the portions of the Aligner buccal and gingival to the bracket. Remove a substantial portion or all of the lingual aspect of the Aligner.

After completion, the process ships the templates, bodies or the completed appliance to the orthodontist either at the onset of treatment or when it is requested.

Figure 4A:
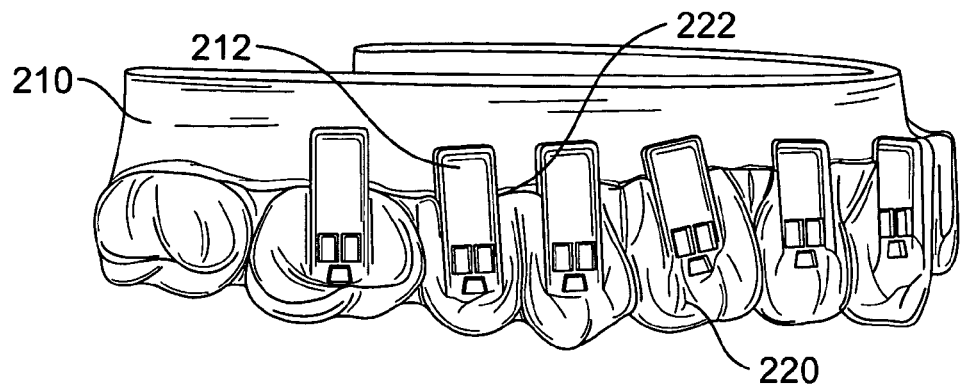
FIGS. 4A–4D show perspective views of various templates.

FIG. 4A shows one embodiment of a dental template 220 or appliance formed over a mold 210. The template looks like a removable appliance; however, it has openings 222 or "portholes" approximating the footprint, key portions of the footprint, and/or possibly other geometrical features of a bracket to guide the precise placement of the bracket on its respective tooth. The template 220 with the openings 222 or "portholes" may also be a guide for enamel etching or adhesive placement.

The mold 210 is a physical rendition of a digital model that has been fabricated using rapid prototyping methods. A bump or projection 212 rises from the mold 210 so when the dental template or appliance is thermal-formed, an opening 222 is formed on the template 220. The opening 222 is where the template is cut out along the edge of the bump or projection 212. The opening 222 has a bracket support edge 226, whose operation is described in more detail in FIG. 4B. In addition to the support edge 226, the template 220 may have features that will minimize the retention of it on the dental anatomy. For example, the lingual side of the device may not have maximum coverage.

Fabrication methods for the mold 210 employ a rapid prototyping device such as a stereolithography machine or a fused deposition modeling machine. A suitable rapid prototyping machine is Model SLA-250/50 available from 3D System, Valencia, Calif. The rapid prototyping machine selectively hardens a liquid or other non-hardened resin into a three-dimensional structure, which can be separated from the remaining non-hardened resin, washed, and used either directly as the appliance or indirectly as a mold for producing the appliance. The prototyping machine receives the individual digital data sets and produces one structure corresponding to each of the desired appliances. Generally, because the stereolithography machine may utilize a resin having non-optimum mechanical properties and which may not be generally acceptable for patient use, the prototyping machine produces the mold 210. After the positive model is prepared, a conventional pressure or vacuum molding machine may be used to produce the appliances from a more suitable material, such as 0.03 inch thermal forming dental material, available from Tru-Tain Plastics, Rochester, Minn. 55902. Suitable pressure molding equipment is available under the trade name BIOSTAR from Great Lakes Orthodontics, Ltd., Tonawanda, N.Y. 14150. The molding machine produces each of the appliances directly from the positive tooth model and the desired material. Suitable vacuum molding machines are available from Raintree Essix, Inc.

In one embodiment, the template is made from a thick material (for example 0.03 inches or more) to provide the user with more guidance in the depth direction. Furthermore, the thick template allows easier lining the bracket to the tooth.

More information on the fabrication of the dental template or appliance is disclosed in U.S. Pat. No. 6,499,997 "Manipulable dental model system for fabrication of a dental appliance"; U.S. Pat. No. 6,497,574 "Modified tooth positioning appliances and methods and systems for their manufacture"; U.S. Pat. No. 6,488,499 "Methods for correcting deviations in preplanned tooth rearrangements"; U.S. Pat. No. 6,485,298 "System and method for releasing tooth positioning appliances"; U.S. Pat. No. 6,471,511 "Defining tooth-moving appliances computationally"; U.S. Pat. No. 6,463,344 "Effic data representation of teeth model"; U.S. Pat. No. 6,457,972 "System for determining final position of teeth"; U.S. Pat. No. 6,454,565 "Systems and methods for varying elastic modulus appliances"; U.S. Pat. No. 6,450,807 "System and method for positioning teeth"; U.S. Pat. No. 6,409,504 "Manipulating a digital dentition model to form models of individual dentition components"; U.S. Pat. No. 6,406,292 "System for determining final position of teeth"; U.S. Pat. No. 6,398,548 "Method system for incrementally moving teeth"; U.S. Pat. No. 6,394,801 "Manipulable dental model system for fabrication of dental appliances"; U.S. Pat. No. 6,390,812 "System and method for releasing tooth positioning appliances"; U.S. Pat. No. 6,386,878 "Systems and methods for removing gingiva from teeth"; U.S. Pat. No. 6,386,864 "Stress indicators for tooth positioning appliances"; U.S. Pat. No. 6,371,761 "Flexible plane for separating teeth models"; U.S. Pat. No. 6,318,994 "Tooth path treatment plan"; U.S. Pat. No. 6,309,215 "Attachment devices and method for a dental appliance"; U.S. Pat. No. 6,299,440 "System and method for producing tooth movement"; U.S. Pat. No. 6,227,851 "Manipulable dental model system for fabrication of a dental appliance"; U.S. Pat. No. 6,227,850 "Teeth viewing system"; U.S. Pat. No. 6,217,325 "Method and system for incrementally moving teeth"; U.S. Pat. No. 6,210,162 "Creating a positive mold of a patient's dentition for use in forming an orthodontic appliance"; and U.S. Pat. No. 5,975,893 "Method and system for incrementally moving teeth," the contents of which are hereby incorporated by reference.

Figure 4B:
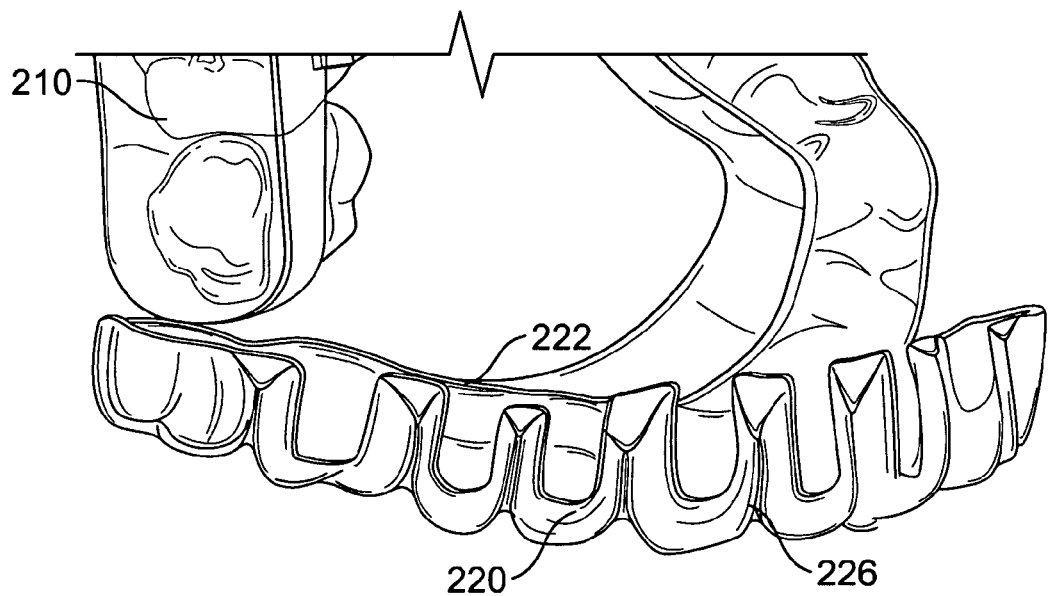

Turning now to FIG. 4B, the template 220 is separated from the mold 210. The opening 222 allows a bracket base to fit into the opening 222. Bracket support edge 226 is needed to securely position the bracket in the template 220. In this embodiment, the bracket support edge 226 is curvaceous. If the edge 226 had been terminated as a simple flat edge, the bracket can be located in X and Y surfaces on the tooth, but the Z direction (buccal lingual direction) would not be controlled. The edge 226 provides the needed control of the bracket's degree of freedom in the Z direction to allow orientation of the bracket about any given axis. Those features allow the bracket to be secured in the proper position and orientation on its respective tooth. The edge 226 can change, depending on vendor-to-vendor or prescription-to-prescription.

Another embodiment of the template can be used for etching bonding chemicals on the patient's teeth. The etching template directs the user to predetermined locations on the teeth surfaces that need to be bonded. The etching template can be either the format of a windowed template or a concave surfaced template where bonding gel is loaded or pre-loaded into the concavity.

Figure 4C:
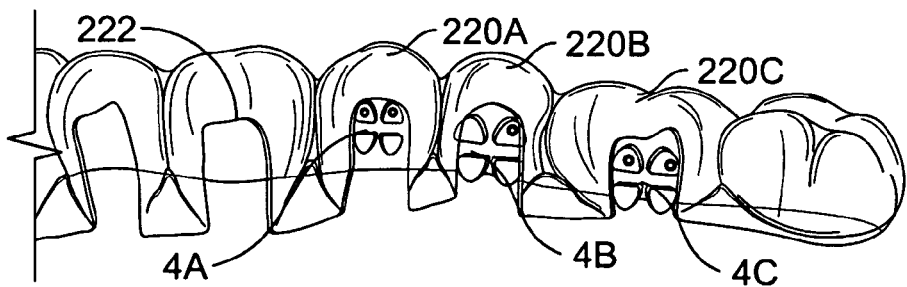

FIG. 4C shows a template wherein each of the openings, cut-outs, port-holes, or slots 222 in the template 220 are designed to fit particular brackets 4A, 4B and a 4C, each of which fits into its respective portion on the template.

Figure 4D:
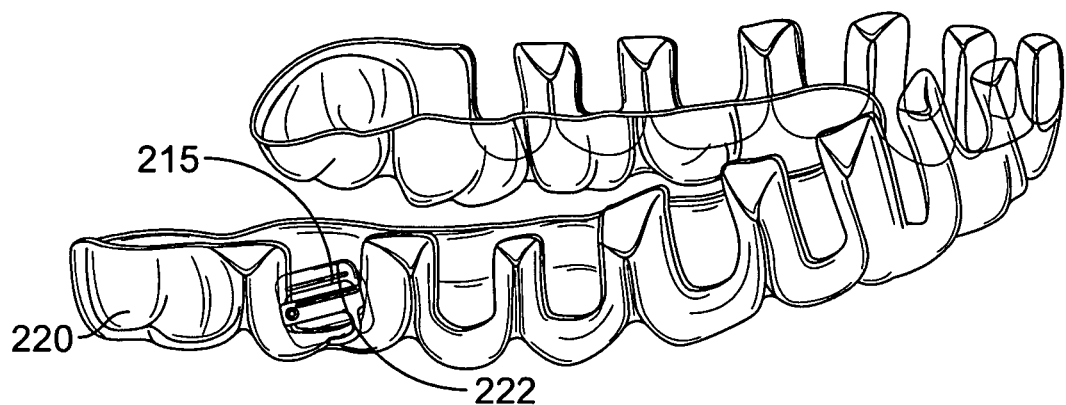

FIG. 4D shows that the system is not limited to bracket design or shape. In FIG. 4D, a molar tube bracket 215 can be placed on the opening 222. Hence, the template 220 is not limited to any specific bracket. Rather, any form of fixed orthodontic appliances placed on a tooth could be accommodated.

Figure 5A:
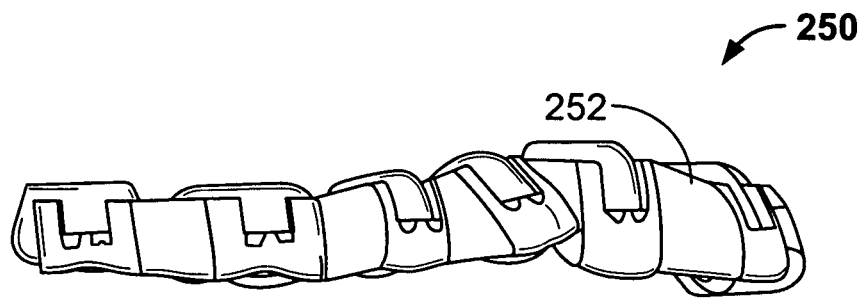
FIGS. 5A and 5B illustrate two embodiments of articulated templates.
Figure 5B:
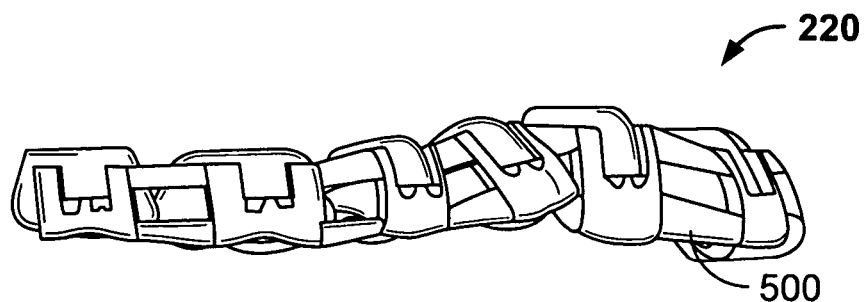

FIGS. 5A and 5B illustrate two exemplary embodiments of articulated templates. FIG. 5A shows two segments joined at the interproximal regions of two adjacent teeth. A number of alternate methods to join the teeth can be used, including that the joining methods could be alternate or vary from one interproximal region to the next. Further, the joining method could also be a layer or layers that cover additional or different surfaces of the teeth as depicted in FIG. 5B.

In FIG. 5A, the template is made up of a number of movable template components 250. Each of the template components 250 can be mounted on a patient's tooth to facilitate bracket bonding. The movable template components 250 are physically linked together by a sheet of material 252 deposited above the components 250 so that they do not break-up or otherwise become disassembled upon removal from its mold or stereolithography apparatus (SLA) model. The articulated templates are advantageous in that they provide greater adjustment flexibility.

The template can additionally be used as an etching template. An etching template allows the doctor to precisely etch the areas of the teeth on which the brackets will be placed. The small windows bound the regions that will be etched to minimize teeth sensitivity to etching or unwanted enamel removal. In another version of the etching template, the cut outs would not be formed. Instead those areas would be concavities facing the tooth surfaces. These concavities would contain an etching compound. The user would expose or activate the etching compound prior to setting the template on the teeth.

The template 220 may be made from materials that contain physical property switches for ease of removal. These switches might include temperature responsive, pH responsive, moisture responsive or a multi-layer system wherein the layers have varying physical properties. The section 500 (FIG. 5B) represents a flexible or pliable material. Additionally, the material could be fiber, cord, fiber mesh, or a fiber-reinforced solid. The interproximal material can be homogenous or heterogeneous.

The template section 252 may be made from materials that contain physical property switches for ease of removal. These switches might include temperature responsive, pH responsive, moisture responsive or a multi-layer system wherein the layers have varying physical properties. The section 252 represents a flexible or pliable material. Additionally, the material could be fiber, cord, fiber mesh, or a fiber-reinforced solid. The interproximal material can be homogenous or heterogeneous.

During one exemplary treatment using both a removable appliance (such as those described in U.S. Pat. No. 6,309,215) and a wire and bracket appliance, a doctor can view the patient's arch(es) that require treatment during a consultation, and then select a particular wire that he/she will use to perform a portion of the treatment. Upon selection of the wire, the doctor submits this information to a virtual setup system based on the doctor's prescription. In another implementation, data mining can use previously stored data to indicate the likelihood of success, and failure rates, of tooth movement using the dental appliances. The data is categorized into three areas to describe the likelihood of successful treatment and movement: for example, a high likelihood of success; a decreased likelihood of success in treatment outcome; and little to no success. Based on the result of the data mining, the system recommends an appropriate sequence of dental appliance usage.

Sequencing is the determination of which aligner feasible movements should be performed first, according to degree of ease or needs for effective treatment outcome. One exemplary implementation of combination treatment performs high-confidence movements earlier in the treatment, followed by more challenging movements. This can mean that removable appliances are used in the first phases of treatment, followed by attachment and wire treatments. Alternatively; attachment and wire treatments can be used first for a case, with removable appliances used in the final phase of treatment. Treatment methods can also be alternated (i.e. aligners, attachments and wires, followed by aligners) and combination treatments can be used simultaneously (i.e. aligners and attachments and wires uses at the same time). Attachments and wires can be placed on the buccal or lingual sides of the teeth. The appliances can also be partial (such as a 3—3 anterior arch), combined with partial attachments and wire treatments (i.e. placed on molars or posterior teeth). In one example iteration, an IPR (interproximal reduction) is used to create space on teeth such as the bicuspid on the upper arch of a patient's jaw. Then, a wire is mounted to pull the anterior teeth back to reduce the arch size and close the interproximal space, followed by 3—3 movement that is achieved using aligners.

Figure 6A:
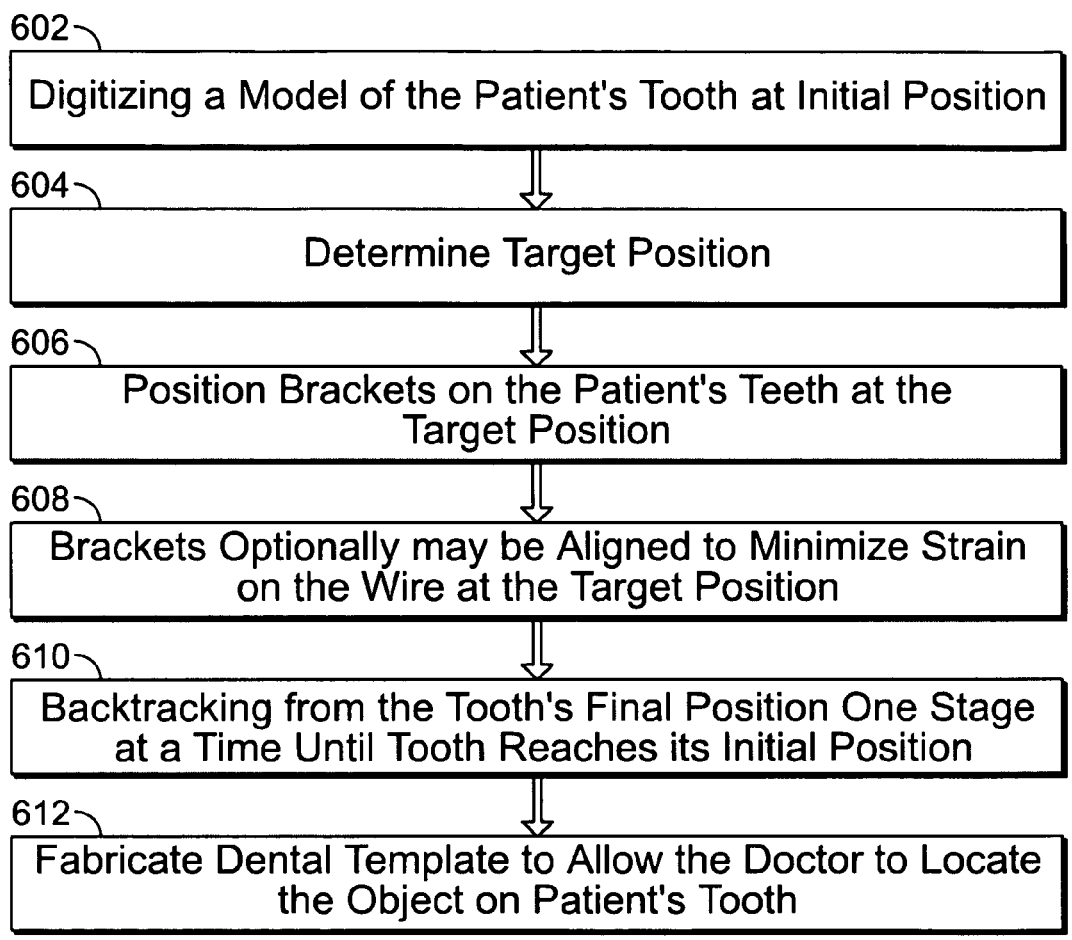
FIG. 6A illustrates a process of fabricating a dental template to position an object on a patient's tooth to move the tooth from an initial position to a target position.

FIG. 6A illustrates a process of fabricating a dental template to position an object (such as a bracket) on a patient's tooth to move the tooth from an initial position to a target position. The process includes digitizing a model of the patient's tooth at the initial position (602). Next, the target position is determined (604). The target position can be a final position for the teeth at the end of the treatment.

Figure 6B:
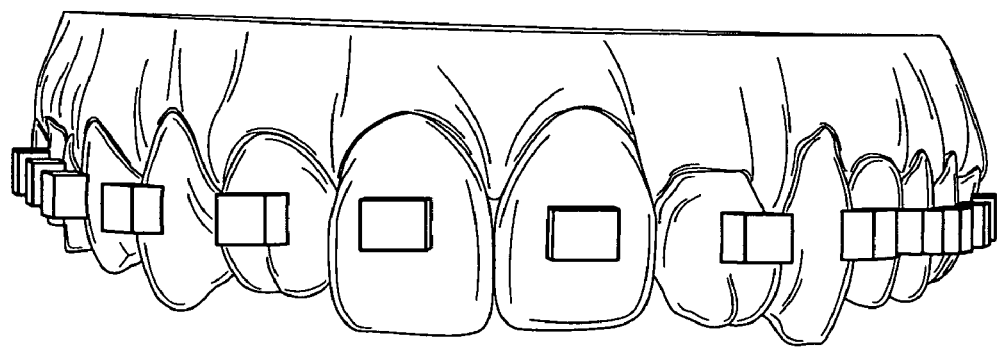
FIG. 6B shows an example of brackets positioned on teeth at their final positions.

Next, after fabrication of the templates the doctor positions a plurality of brackets on the patient's teeth at the target position, each bracket having a slot adapted to receive an orthodontic wire passing therethrough (606) as illustrated in FIG. 6B showing the mounted brackets on the final position of the patient's teeth. The process optionally aligns the brackets to minimize strain on the wire at the target position (608).

The process determines the position of the object at the initial position by backtracking from the tooth's final position one stage at a time until tooth reaches its the initial position (610). The coordinate transformation for moving the tooth from its final position to its initial position is applied to determine the position of the object's initial position.

Figure 6C:
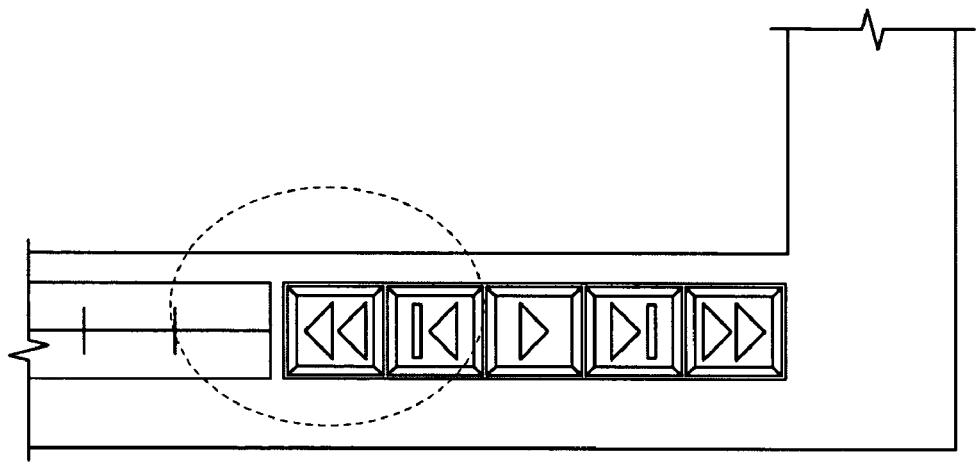
FIG. 6C shows an exemplary user interface that allows a user to visualize teeth at each treatment stage.
Figure 6D:
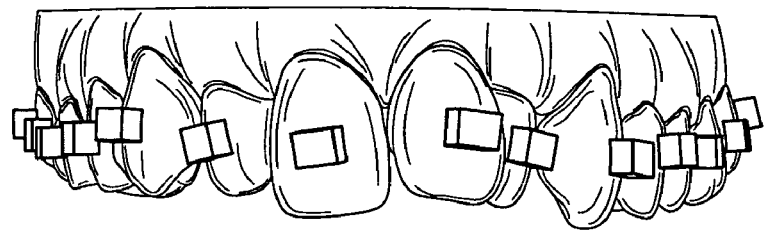
FIG. 6D shows the exemplary brackets when backtracked into their initial positions.

FIG. 6C shows an exemplary user interface that allows a user to visualize teeth at each treatment stage. In one example, the teeth can be backtracked one stage at a time to arrive at the initial positions. Since the brackets are secured to the teeth, the backtracked position of the brackets can also be determined. FIG. 6D shows the exemplary brackets when backtracked into their initial positions. The process can also determine a deviation of the object from an ideal placement and iteratively adjust the position of the object to minimize the deviation.

Referring back to FIG. 6A, finally, the dental template is fabricated to allow the doctor to locate the object on the patient's tooth (612). The template can be fabricated using a rapid prototyping method. One or more bracket objects can be embedded in the dental template and the dental template can be inserted over the patient's teeth. Alternatively, the bracket objects can be inserted into an opening on the dental template prior to being bonded on the teeth.

Figure 7:
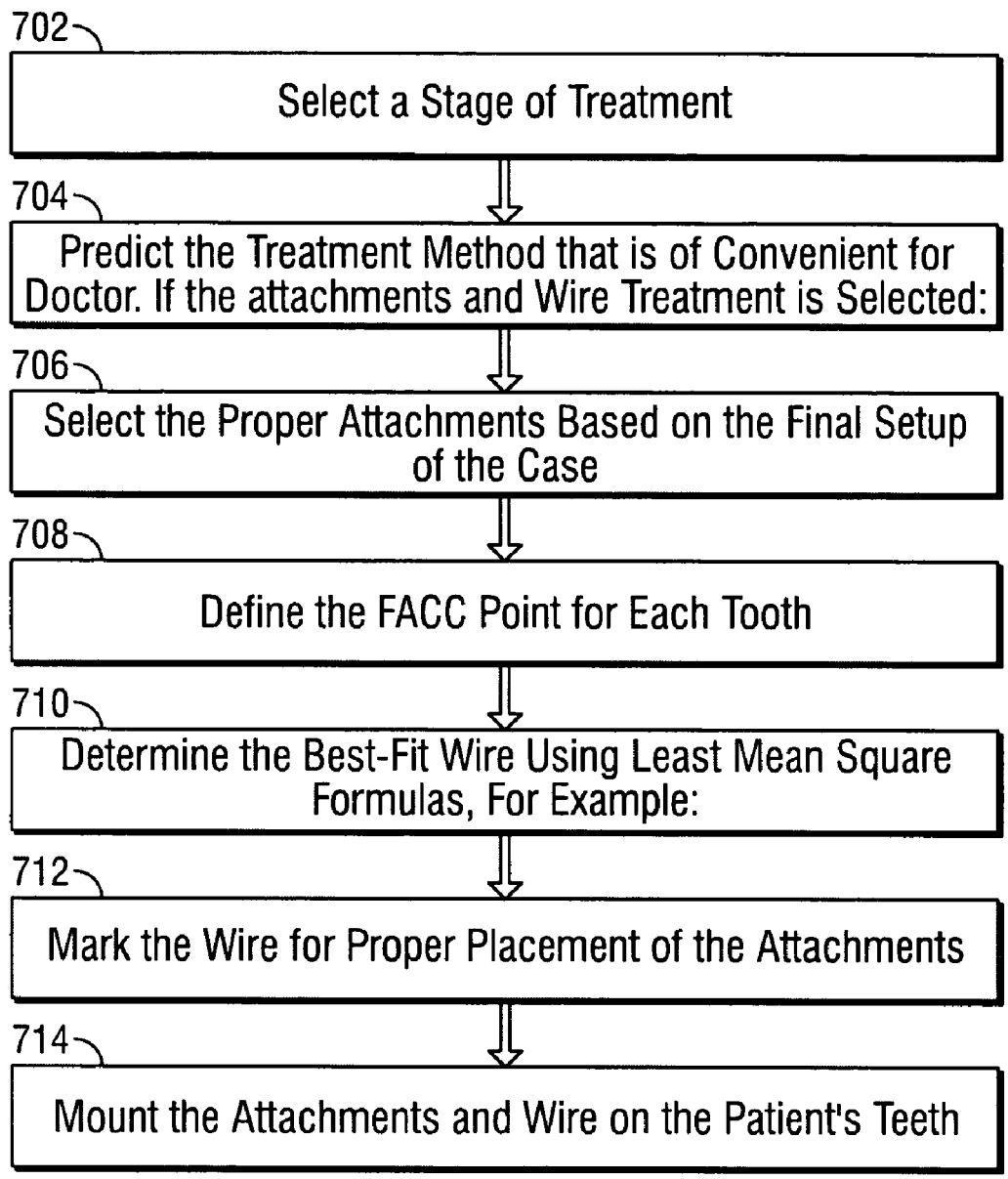
FIG. 7 is a diagram of a process to attach an object on a tooth.

FIG. 7 describes one exemplary implementation of Combination Treatments. A stage of treatment is selected (step 702). The process makes a prediction of a treatment that is convenient for the doctor, to use either a removable appliance for treatment or to use attachments and wires (step 704).

Based on the final setup of the case, the proper attachments are selected (step 706). Once the attachments are determined, a predetermined fit value such as a FACC point is defined (step 708). Factors included in the determination of the FACC point include teeth, attachment, and wire collisions. Once the FACC point is determined, the database provides the best-fit wire for use by the doctor (step 710). Dental practitioners use individual approaches when selecting wires for patients. Some doctors use a single type of wire, others choose from a number of different wires. Alternatively, a standard wire can be used. Once selected, the wire is marked for proper placement of the attachments (step 712). Finally, the attachments and wire(s) are mounted on the patient's teeth (step 714).

Figure 8:
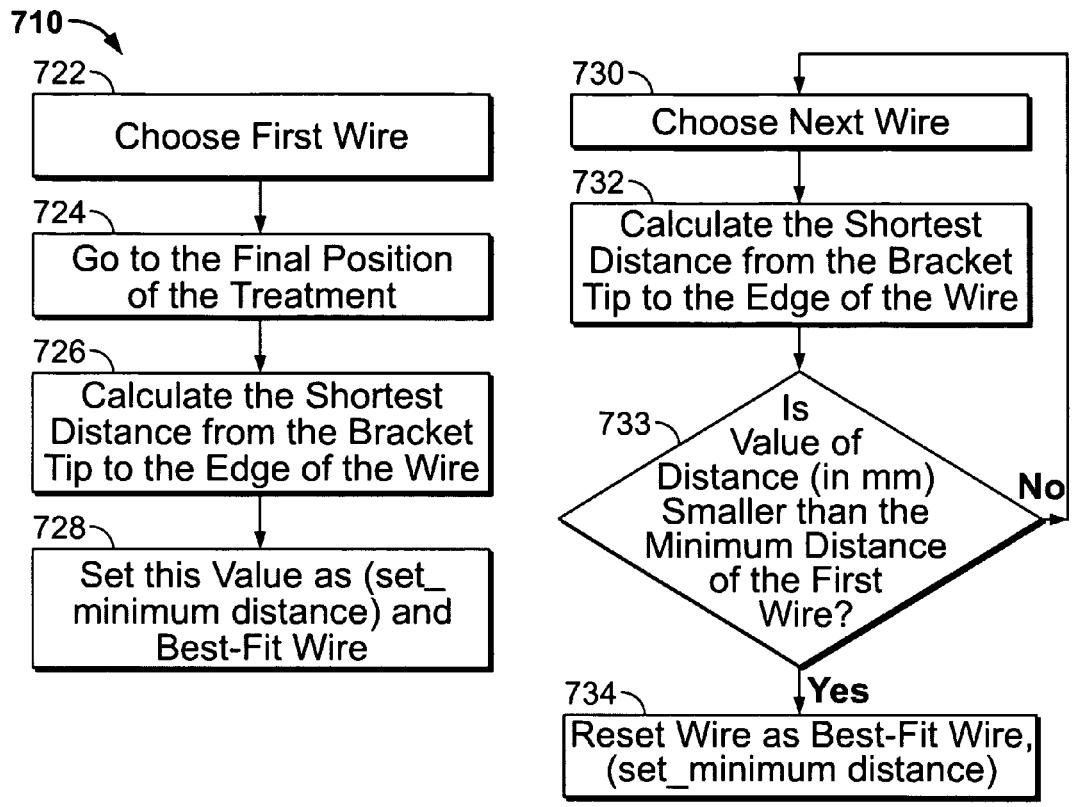
FIG. 8 is a diagram of a process to fit wire on the teeth.

FIG. 8 describes Step 710. The best-fit wire is determined using a series of simple least mean square mathematical formulas. Given a particular patient case (step 722), a wire is selected. Using the final position of the treatment (step 724), the shortest distance from the bracket tip to the edge of the wire is calculated (726).

Let d=distance between the attachment and the wire,

For any i=1–16 or 17–32, depending on which tooth/jaw, $$d_i > 0$$

$$d_i < D$$

where D is a number defined to be between 0.1 mm and 50 mm. This wire is set as the best-fit wire, with the minimum distance between the attachments and wire (728). All subsequent wires are measured using the same calculations (730–734).

Figure 9:
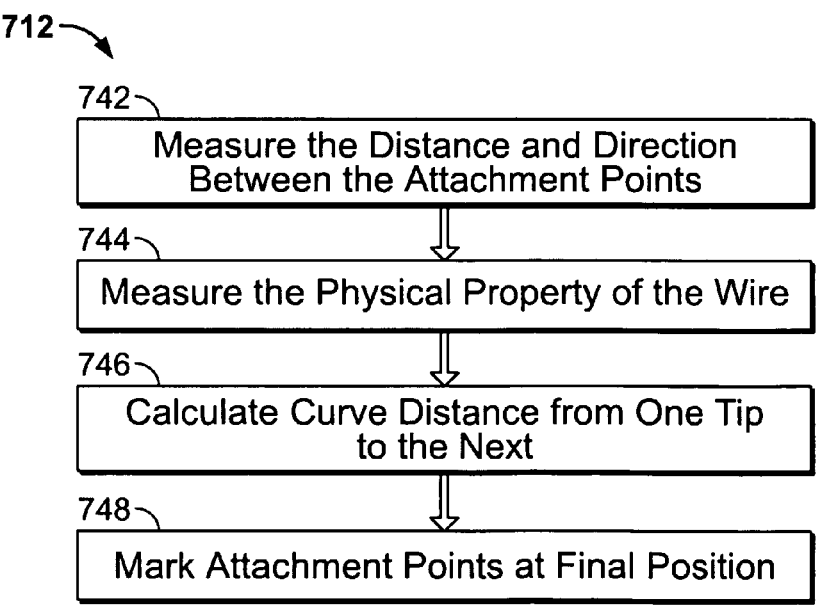
FIG. 9 is a diagram illustrating the marking of a wire for attachment placement.

FIG. 9 describes more detail step 712, marking the wire for attachment placement by the doctor. Measurements are retrieved from the placement of the attachments on the jaw at the initial position. Distance and direction are measured between the points (742). Two additional areas can be measured: 1) the physical property of the wire, i.e. how much wire can bend (step 744), and 2) the curve distance from one bracket tip to the next (step 746). Finally, points are placed on the wire to show the place where the first attachment stops (step 748). The same iteration is repeated with each subsequent attachment.

Figure 10:
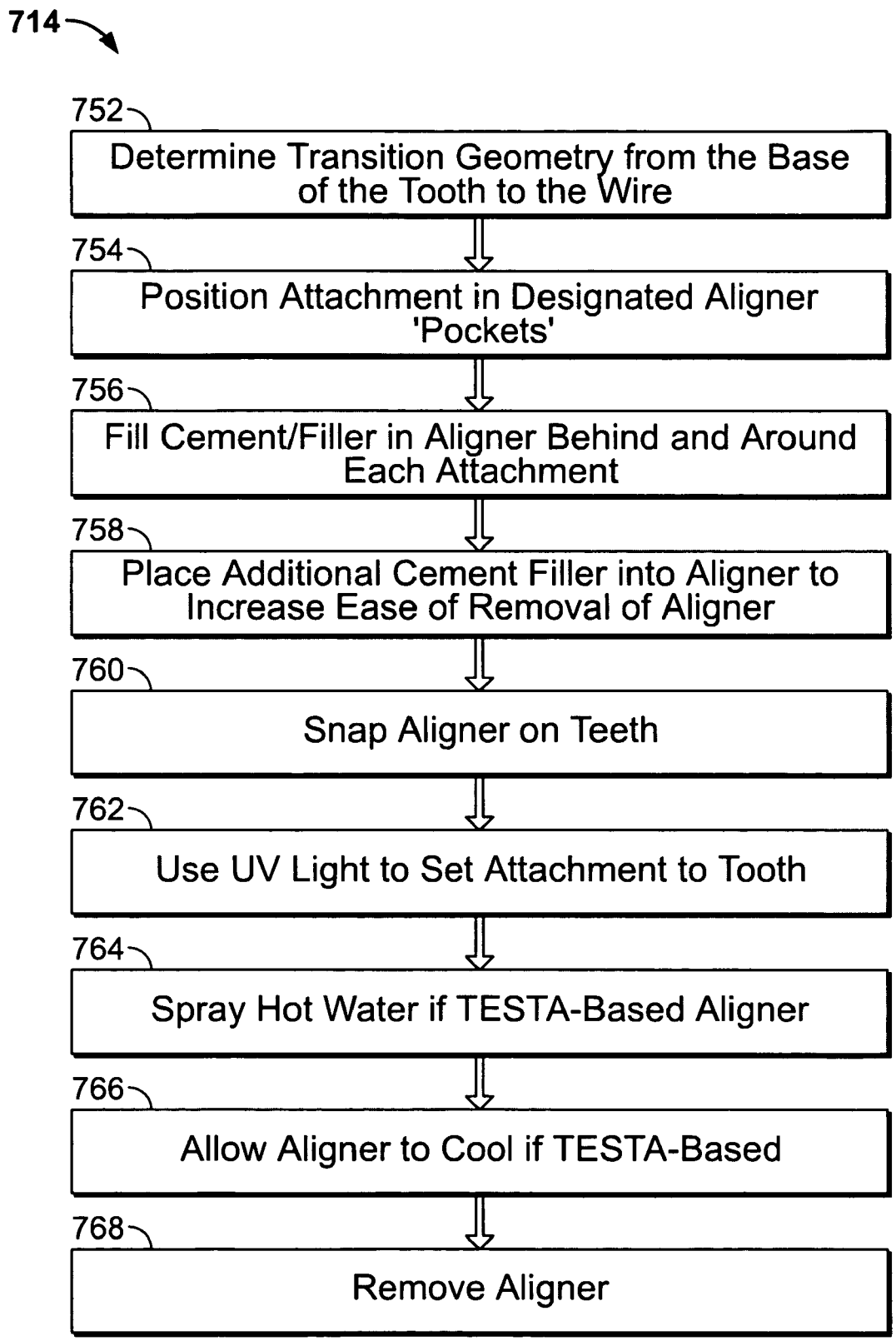
FIG. 10 is a diagram illustrating attachment mounting using the dental template.

FIG. 10 describes in more detail step 714. To mount the wire and attachments, transition geometry is determined from the base of the tooth to the wire (752). Attachment object is placed inside the pocket area of the aligner (754). The filler material, most likely cement, is placed in the aligner behind the attachment and in the remaining aligner area (756 and 758). This increases ease of removal of the aligner at the later stages when the attachments are placed on the teeth. The doctor snaps the aligner with the attachment and cement on the teeth (760). Ultraviolet light is used to secure the cement filler material to the teeth (762). For Testa based aligners, hot water is sprayed on the aligner (step 764) because the Testa material responds to the heat by becoming more pliable. Once the aligner has cooled (766), the doctor can remove it from the patient's mouth with relative ease (768). The attachment(s) are now fastened to the teeth, which follows standard orthodontics principles of placing brackets. Finally, the doctor connects the wire to each attachment using the designations that were marked on the wire in step 712 as a reference.

Exemplary pseudo-code to perform a combination treatment is as follows:

Select a stage of treatment.
Make a prediction to use attachments and wires treatment based on highest degree of convenience for doctor.
Select the proper attachments based on the final setup of the case.
Define the FACC point.
Use least mean square formulas to determine the best-fit wire.
 Choose a wire.
 Go to the final position of treatment.
 Calculate the shortest distance from the bracket tip to the edge of the wire.
 Set this value as (set_minimum distance) and best-fit wire.
 Choose next wire.
 Calculate the shortest distance from the bracket tip to the edge of the wire.
  If value of distance (in mm) is smaller than the minimum distance of the first wire, this wire is reset as best-fit wire.
  If value of distance (in mm) is larger, the first wire is selected as the best-fit.
Mark the wire for proper placement of the attachments.
 Measure the distance and direction between the attachment points.
 Measure the physical property of the wire.
 Calculate curve distance from one tip to the next.
 Mark attachment points at final position.
 If points are acceptable, repeat this iteration for each subsequent attachment.
Mount the wire and attachments on the patient's teeth.
 Determine transition geometry from the base of the tooth to the wire.
 Position attachment in designated aligner 'pockets'.
 Fill cement/filler in aligner behind and around each attachment.
 Place additional cement filler into aligner to increase ease of removal of aligner.
 Snap aligner on teeth.
 Use UV light to set attachment to tooth.
 Spray hot water on Testa-based aligner.
 Allow aligner to cool.
 Remove aligner.

Thus, the above process determines an optimum treatment sequence based on historical data; and fabricating one or more dental devices to move teeth, the devices being selected from either a computer-synthesized retainer or a combination of attachments and wire. The determining of an optimum treatment sequence can include capturing a digital model of a patient's teeth; and comparing the digital model to a library of historical treatment cases. The treatment can include moving teeth using the retainers and at the end of treatment with aligners, fabricate a retainer with the attachments embedded therein.

Various alternatives, modifications, and equivalents may be used in lieu of the above components. Additionally, the techniques described here may be implemented in hardware or software, or a combination of the two. The techniques may be implemented in computer programs executing on programmable computers that each includes a processor, a storage medium readable by the processor (including volatile and nonvolatile memory and/or storage elements), and suitable input and output devices. Program code is applied to data entered using an input device to perform the functions described and to generate output information. The output information is applied to one or more output devices. Each program can be implemented in a high level procedural or object-oriented programming language to operate in conjunction with a computer system. However, the programs can be implemented in assembly or machine language, if desired. In any case, the language may be a compiled or interpreted language. Each such computer program can be stored on a storage medium or device (e.g., CD-ROM, hard disk or magnetic diskette) that is readable by a general or special purpose programmable computer for configuring and operating the computer when the storage medium or device is read by the computer to perform the procedures described. The system also may be implemented as a computer-readable storage medium, configured with a computer program, where the storage medium so configured causes a computer to operate in a specific and predefined manner. Further, while the invention has been shown and described with reference to an embodiment thereof, those skilled in the art will understand that the above and other changes in form and detail may be made without departing from the spirit and scope of the following claims.

What is claimed is:

1. A method of fabricating a dental template to position a plurality of brackets on a patient's teeth to move at least one of the teeth from an initial position to a subsequent position, the method comprising:
   providing a digital model of the patient's teeth in their initial positions;
   determining a target position for each of the brackets on the digital teeth model;
   creating a bracketed model comprising placing virtual representations of the brackets on the digital teeth model at the target positions;
   creating a scaled teeth model by scaling up the digital teeth model;
   locating the bracketed model within the volume of the scaled teeth model;
   generating a template model, the generating comprising removing a volume from the scaled teeth model corresponding to the volume of the located bracketed model so as to create teeth receiving cavities within the scaled teeth model, and further removing portions of the scaled teeth model so as to create a plurality of openings to the positions of the virtual brackets; and
   directly fabricating the dental template from the template model, wherein the template comprises multiple openings, each opening configured to guide a bracket into the target position on one of the patient's teeth after the template is placed over the patient's teeth.

2. The method of claim 1, further comprising determining a target orientation for each of the brackets to position a slot of each bracket to receive an orthodontic wire, wherein the template is configured to orient the brackets on the patient's teeth.

3. The method of claim 2, wherein
   each bracket includes a slot adapted to receive an orthodontic wire passing therethrough, and wherein
   the target orientations for the brackets are determined to minimize strain on the wire when the teeth are moved from initial to subsequent positions.

4. The method of claim 3, wherein the wire is arch-shaped when the teeth are in their subsequent positions and irregular when the teeth are in their initial positions.

5. The method of claim 1, further comprising allowing a user to change the position of at least one of the brackets away from its target position on the digital tooth model, before fabricating the template.

6. The method of claim 5, further comprising determining a deviation of at least one of the brackets from an ideal placement and iteratively adjusting the position of the bracket to minimize the deviation.

7. The method of claim 1, wherein fabricating comprises rendering a physical dental template using a rapid prototyping method.

8. The method of claim 1, wherein the openings are configured so that the brackets can be inserted into the openings after the template is placed over the patient's teeth.

9. The method of claim 1, the at least one opening of the template configured such that a bracket on the patient's tooth is positionable in the at least one opening and the bracket is movable through an open gingival side of the at least one opening during removal of the template from the patient's teeth.

10. A method of positioning a bracket on a patient's tooth, the method comprising:
   providing a dental template of claim 1 for positioning of one or more brackets on a patient's teeth, the template configured to fit over a plurality of the patient's teeth and for each of at least a plurality of teeth the template has a first surface fixed in shape and designed to be disposed opposite a corresponding surface of the tooth, wherein the first surface of the template and the corresponding surface of the tooth have approximately matching three-dimensional geometries, the first surface of the template having an opening comprising a cut-out that is open to a gingival side of the template, the opening being configured to guide the bracket into position on the tooth;
   fitting the template on the patient's teeth; and
   positioning a bracket on the patient's tooth comprising positioning the bracket in the opening and in contact with the patient's tooth.

11. A method for fabricating a dental template to position a bracket on a patient's tooth, the method comprising:
   providing a digital model of the patient's tooth at an initial tooth position;
   providing a final position for the tooth on the digital model;
   placing a virtual representation of the bracket on the tooth in its final position;
   determining a location of the bracket on the tooth in its initial position by backtracking from the placement of the bracket on the tooth in its final position;
   creating a scaled digital model of the tooth by scaling up the digital model;
   generating a template model, the generating comprising removing a volume from the scaled tooth model corresponding to the volume of the digital model and positioned bracket so as to create teeth receiving cavities within the scaled tooth model, and further removing a portion of the scaled tooth model so as to create an opening to the backtracked position of the bracket representation; and
   fabricating a dental template from the template model.

12. The method of claim 11, wherein fabricating comprises rendering a physical dental template using a rapid prototyping method.

13. The method of claim 11, wherein the template is articulable with a plurality of flexibly linked cavities.

14. The method of claim 11, wherein the bracket guiding opening is configured so that the bracket can be inserted into the opening after the template is placed over the tooth.

15. The method of claim 11, further comprising rendering simulated teeth movement over time.

16. The method of claim 11, further comprising treating teeth using a combination of removable and fixed appliances.

17. The method of claim 16, wherein the fixed appliance covers two or more teeth on an arch.

18. The method of claim 16, wherein the fixed appliance is positioned on a lingual side of the patient's teeth.

19. A method for fabricating a dental template for positioning a plurality of orthodontic brackets on a patient's teeth, the method comprising:
   providing a digital model of the patient's teeth in their initial positions;
   determining a target position on the digital teeth model for positioning of each of one or more virtual brackets;
   creating a scaled teeth model by scaling up the digital teeth model;

generating a template model, the generating comprising
removing a volume from the scaled teeth model corresponding to the volume of the digital teeth model and positioned virtual brackets so as to create teeth receiving cavities within the scaled teeth model, and further removing portions of the scaled teeth model so as to create a plurality of openings to the target positions of the brackets; and fabricating the dental template from the template model.

20. The method of claim 19, wherein positioning a digital model of each bracket at its target position comprises creating a bracketed teeth model comprising the digital teeth model and the bracket models.

21. The method of claim 19, further comprising locating the digital teeth model within the volume of the scaled teeth model.

22. The method of claim 19, further comprising determining a target orientation for each of the brackets to position a slot of each bracket to receive an orthodontic wire, wherein the template is configured to orient the brackets on the patient's teeth.

23. The method of claim 19, wherein fabricating comprises rendering a physical dental template using a rapid prototyping method.

* * * * *